US006569650B1

(12) United States Patent
Merkamm et al.

(10) Patent No.: US 6,569,650 B1
(45) Date of Patent: May 27, 2003

(54) PROCESS FOR THE FERMENTATIVE PREPARATION OF METABOLIC PRODUCTS AND FOR THE NUCLEOTIDE SEQUENCES ENCODING FOR THE SOD GENE

(75) Inventors: Muriel Merkamm, Les Ulis (FR); Armel Guyonvarch, Orsay (FR); Achim Marx, Bielefeld (DE)

(73) Assignee: Degussa AG, Dusseldorf (DE)

( * ) Notice: Subject to any disclaimer, the term of this patent is extended or adjusted under 35 U.S.C. 154(b) by 0 days.

(21) Appl. No.: 09/373,731

(22) Filed: Aug. 13, 1999

(51) Int. Cl.[7] ................................................. C12P 13/04
(52) U.S. Cl. .................. 435/106; 435/115; 435/320.1; 435/252.32; 536/23.1; 536/23.2; 536/23.7
(58) Field of Search ............... 536/23.1, 23.2; 435/252.32, 320.1, 106, 115

(56) References Cited

U.S. PATENT DOCUMENTS 4,529,697 A      7/1985   Yoshimura et al.
5,179,010 A      1/1993   Yoshihara et al.
5,525,463 A  *   6/1996   Zolg ............................. 435/6

FOREIGN PATENT DOCUMENTS

EP       1 108 790       6/2001
WO       WO 01/00804     1/2001

* cited by examiner

Primary Examiner—Ponnathapu Achutamurthy
Assistant Examiner—Kathleen Kerr
(74) Attorney, Agent, or Firm—Pillsbury Winthrop LLP (57) ABSTRACT

The present invention is directed to nucleotide sequences coding for the superoxide dismutase (sod) gene from *Corynebacterium melassecola*. It includes processes for the fermentative preparation of nucleotides, vitamins and L-amino acids using coryneform bacteria in which the sod gene is amplified.

12 Claims, 2 Drawing Sheets

PROCESS FOR THE FERMENTATIVE PREPARATION OF METABOLIC PRODUCTS AND FOR THE NUCLEOTIDE SEQUENCES ENCODING FOR THE SOD GENE

BACKGROUND OF THE INVENTION

1. Field of the Invention

The invention provides nucleotide sequences encoding for the superoxide dismatase (sod) gene and a process for the fermentative preparation of nucleotides, vitamins and L-amino acids, in particular L-lysine using coryneform bacteria in which the sod gene is amplified.

2. Background Information

Nucleotides, vitamins and L-amino acids, in particular L-lysine, are used in the foodstuffs industry, in animal nutrition, in human medicine and in the pharmaceutical industry.

It is known that these substances can be prepared by fermentation of strains of coryneform bacteria, in particular *Corynebacterium glutamicum*. Constant efforts are made to improve the method of preparation due to the high degree of importance of these substances. Process improvements may relate to fermentation engineering factors such as e.g. stirring and supplying with oxygen, or the composition of the nutrient medium, such as e.g. the sugar concentration during fermentation, or the working up process aimed at obtaining the product itself by e.g. ion exchange chromatography or the intrinsic power of the microorganism itself.

To improve the power of the microorganisms, the methods of mutagenesis, selection and mutant choice are used. Strains which are resistant to antimetabolites or which are auxotrophic for significant regulatory intermediates are obtained in this way and produce nucleotides, vitamins and amino acids.

For some time now the methods of recombinant DNA engineering have also been used for the strain-improvement of L-amino acid-producing strains of *Corynebacterium glutamicum*, by amplifying individual amino acid biosynthetic genes and investigating the effect on L-amino acid production.

U.S. Pat. No. 5,179,010 describes strains of coryneform bacteria which are e.g. resistant to methylviologen or benzoyl peroxide, have an increased activity to superoxide dismutase and have an improved lysine yield. These strains were produced by non-targeted mutagenesis using the mutagen N-methyl-N-nitro-N-nitrosoguanidine. The increase in the concentration of superoxide dismutase in the strains mentioned there was at most 56%.

U.S. Pat. No. 4,529,697 describes mutants of coryneform bacteria which produce glutamic acid. The increase in the concentration of superoxide dismutase in the strains mentioned there was at most 105%.

SUMMARY OF THE INVENTION

The inventor has formulated the object as the provision of new steps for the improved handling of superoxide dismutase from coryneform bacteria. These steps can be used during the fermentative preparation of nucleotides, vitamins and L-amino acids, in particular L-lysine.

DETAILED DESCRIPTION OF THE INVENTION

Nucleotides, vitamins and L-amino acids, in particular L-lysine, are used in the foodstuffs industry, in animal nutrition, in human medicine and in the pharmaceutical industry. Lysine-producing strains of coryneform bacteria are known from the prior art, in which the concentration of superoxide dismutase is increased by 27 to 56% and which liberate amplified lysine. These strains were obtained by non-targeted mutagenesis.

Whenever L-lysine or lysine is mentioned in the following this is intended to mean not only the base but also salts such as, for example, lysine monohydrochloride or lysine sulfate.

The invention provides a preferably recombinant DNA from the Corynebacterium source which can replicate in coryneform microorganisms and which contains at least the nucleotide sequence which encodes for the sod gene represented in SEQ-ID-No.1.

The invention also provides a replicable DNA in accordance with Claim 1 comprising:

(i) the nucleotide sequence, shown in SEQ-ID-No.1, or (ii) at least one sequence which corresponds to the sequence (i) within the region of degeneration of the genetic code, or (iii) at least one sequence which hybridizes with the sequence which is complementary to sequence (i) or (ii) and optionally (iv) functionally neutral sense mutations in (i).

Coryneform microorganisms, in particular the strain Corynebacterium, transformed by the introduction of the replicatable DNA mentioned above, are also provided by the invention.

Furthermore the invention provides a process for the fermentative preparation of nucleotides, vitamins and L-amino acids, in particular L-lysine, using coryneform bacteria which in particular already produce the relevant product and in which the nucleotide sequences encoding for the sod gene are amplified, in particular are overexpressed.

The expression "amplification" in this connection describes the increase in the intracellular activity of one or more enzymes in a microorganism which are encoded by the corresponding DNA, for example by increasing the copy number of the gene or genes, using a strong promoter or a gene which encodes for a corresponding enzyme with high activity and optionally combining these steps.

The microorganisms which are the subject of the present invention can produce nucleotides, vitamins and L-amino acids, in particular L-lysine, from glucose, saccharose, lactose, fructose, maltose, molasses, starch, cellulose or from glycerol and ethanol. They may be members of the coryneform bacteria family in particular the genus Corynebacterium. In the case of the Corynebacterium genus, in particular the species *Corynebacterium glutamicum*, it should be mentioned that this is well-known in the specialist field for its ability to produce L-amino acids.

Suitable strains of the genus Corynebacterium, in particular the species *Corynebacterium glutamicum* are for example the known wild-type strains

*Corynebacterium glutamicum* ATCC13032
*Corynebacterium acetoglutamicum* ATCC15806
*Corynebacterium acetoacidophilum* ATCC13870
*Corynebacterium ammoniagenes* ATCC6871
*Corynebacterium thermoaminogenes* FERM BP-1539
*Brevibacterium flavum* ATCC14067
*Brevibacterium lactofermentum* ATCC13869 and
*Brevibacterium divaricatum* ATCC14020

*Corynebacterium melassecola* ATCC17965

*Brevibacterium ammoniagenes* IFO12072 and mutants or strains prepared therefrom which can produce nucleotides, vitamins and L-amino acids, such as for example the 5'-inosinic acid-producing strains

*Corynebacterium ammoniagenes* ATCC15190

*Corynebacterium ammoniagenes* ATCC15454

*Corynebacterium glutamicum* ATCC14998 or such as for example the 5'-guanylic acid-producing strains

*Corynebacterium glutamicum* ATCC21171 or

*Corynebacterium ammoniagenes* ATCC19216 or such as for example the L-lysine producers

*Corynebacterium glutamicum* FERM-P 1709

*Brevibacterium flavum* FERM-P 1708

*Brevibacterium lactofermentum* FERM-P 1712

*Corynebacterium glutamicum* FERM-P 6463 and

*Corynebacterium glutamicum* FERM-P 6464

*Corynebacterium glutamicum* DSM 5714.

The inventors were able to isolate the new sod gene from *Corynebacterium melassecola* ATCC17965.

Here, the superoxide dismutase enzyme protein was first purified to homogeneity using chromatographic methods. Methods and instructions for protein purification and preparation are fully described e.g. in the textbook by Schleifer and Wensink: Practical Methods in Molecular Biology (Springer Verlag, Berlin, Germany, 1981), in the manual by Harris and Angal: Protein Purification Methods: A Practical approach (IRL Press, Oxford, UK, 1989), in the textbook by Scopes: Protein Purification: Principles and Practice, 3rd ed. (Springer Verlag, New York, USA, 1993) and in generally well-known textbooks and manuals. The pure enzyme protein can then be broken down into peptides by treating with suitable enzymes such as e.g. trypsin or chymotrypsin. The amino acid sequence in these peptides can be determined by the method of N-terminal sequencing described by Edman (Archives of Biochemistry 22, 475, (1949)). Methods and instructions for protein sequencing are given e.g. in Smith: Protein Sequencing Protocols: Methods in Molecular Biology, Vol. 64 and Vol. 112 (Humana Press, Totowa, N.J., USA, 1996) and in Kamp et al.: Protein Structure Analysis: Preparation, Characterization and Microsequencing (Springer Verlag, New York, N.Y., USA, 1997). The amino acid sequence in the superoxide dismutase enzyme protein can be partly or completely determined in this way, depending on the degree of complexity.

By exploiting the known use of a codon for coryneform bacteria (Malumbres et al. (Gene 134, 15–24 (1993)), synthetic oligonucleotides can be synthesized and used as primers for amplifying the corresponding chromosomal DNA segments by means of the polymerase chain reaction (PCR). Instructions for this can be found by a person skilled in the art, inter alia, for example in the manual by Gait: Oligonucleotide Synthesis: A Practical Approach (IRL Press, Oxford, UK, 1984) and in Newton and Graham: PCR (Spektrum Akademischer Verlag, Heidelberg, Germany, 1994). The DNA fragment of the sod gene obtained in this way is then cloned using known methods such as described e.g. in Sambrook et al.: Molecular Cloning: A Laboratory Manual 2nd ed. (Cold Spring Harbor Laboratory Press, USA, 1989) and can be used as probes for testing the complete gene including its 5' and 3' flanks in gene banks.

The construction of gene banks is described in generally well-known textbooks and manuals. The following may be mentioned as examples, the textbook by Winnacker: Gene und Klone, Eine Einfuhrung in die Gentechnologie (Verlag Chemie, Weinheim, Germany, 1990) or the manual by Sambrook et al.: Molecular Cloning, A Laboratory Manual (Cold Spring Harbor Laboratory Press, 1989). A very well known gene bank is that of *E. coli* K-12 strain W3110 which was constructed by Kohara et al. (Cell 50, 495–508 (1987)) in λ-vectors. Bathe et al. (Molecular and General Genetics, 252:255–265, 1996) describe a gene bank of *C. glutamicum* ATCC13032, which was constructed with the aid of the cosmid vector SuperCos I (Wahl et al., 1987, Proceedings of the National Academy of Sciences USA, 84:2160–2164) in *E. coli* K-12 strain NM554 (Raleigh et al., 1988, Nucleic Acids Research 16:1563–1575). Bormann et al. (Molecular Microbiology 6(3), 317–326)) also describe a gene bank of *C. glutamicum* ATCC13032 using the cosmid pHC79 (Hohn and Collins, Gene 11, 291–198 (1980)). To produce a gene bank of *C. glutamicum* in *E. coli*, plasmids such as pBR322 (Bolivar, Life Sciences, 25, 807–818 (1979)) or pUC9 (Vieira et al., 1982, Gene, 19:259–268) may also be used. Suitable hosts are in particular those *E. coli* strains which are restriction and recombination defective. An example of these is the strain DH5αmcr described by Grant et al. (Proceedings of the National Academy of Sciences USA, 87, (1990) 4645–4649). The long DNA fragments cloned with the aid of cosmids can then again be sub-cloned in vectors currently used for sequencing and then sequenced as is described e.g. in Sanger et al. (Proceedings of the National Academy of Sciences of the United States of America USA, 74:5463–5467, 1977).

The DNA sequences obtained can then be tested with known algorithms or sequence analysis programs such as e.g. that of Staden (Nucleic Acids Research 14, 217–232 (1986)), the GCG program by Butler (Methods of Biochemical Analysis 39, 74–97 (1998)) the FASTA algorithm of Pearson and Lipman (Proceedings of the National Academy of Sciences USA 85, 2444–2448 (1988)) or the BLAST algorithm of Altschul et al. (Nature Genetics 6, 119–129 (1994)) and compared with the sequence registers present in publicly accessible data banks. Publicly accessible banks for nucleotide sequences are for example those in the European Molecular Biologies Laboratories (EMBL, Heidelberg, Germany) or those in the National Center for Biotechnology Information (NCBI, Bethesda, Md., USA).

The new DNA sequences of *C. glutamicum* encoding for the sod gene which was obtained in this way is a constituent of the present invention as SEQ ID NO 1. Furthermore the amino sequence of the corresponding protein was derived from the DNA sequence present. The amino acid sequence of the sod gene product is represented in SEQ ID NO 2.

Encoding DNA sequence which was produced from SEQ ID NO 1 by the degenerability of the genetic code is also a constituent of the invention. In the same way DNA sequences which hybridize with SEQ ID NO 1 or parts of SEQ ID NO 1 are also a constituent of the invention. In the specialist field, furthermore, conservative amino acid exchanges such as e.g. the exchange of glycine for alanine or of aspartic acid for glutamic acid in proteins, as "sense mutations", are also known and do not lead to any basic modification in the activity of the protein i.e. they are functionally neutral. Furthermore, it is known that changes to the N and/or C terminus of a protein cannot substantially impair or even stabilize its function. Data relating to this can be found by a person skilled in the art, inter alia, in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in well-known textbooks on genetics and molecular biology.

Amino acid sequences which are produced in a corresponding manner from SEQ ID NO 2 are also a constituent of the invention.

Amplification of the sod gene in coryneform bacteria leads to an unusually high increase in the superoxide dismutase concentration in the microorganism.

To produce an overexpression, the copy number of the corresponding gene can be increased, or the promoter and regulation region or the ribosome bonding site, which is located upstream of the structure gene, can be mutated. Expression cassettes, which are incorporated upstream of the structure gene, operate in the same way. It is also possible to increase expression during the course of fermentative L-lysine production with inducible promoters. Expression is also improved by measures aimed at prolonging the lifetime of m-RNA. Furthermore, enzyme activity can also be amplified by inhibiting degradation of the enzyme protein. The genes or gene constructs can either be present in plasmids with different copy numbers or be integrated and amplified in the chromosome.

Alternatively, overexpression of the relevant genes may also be achieved by modifying the composition of the media and management of the culture.

Instructions for these procedures may be found by a person skilled in the art, inter alia, in Martin et al. (Bio/Technology 5, 137–146 (1987)), in Guerrero et al. (Gene 138, 35–41 (1994)), Tsuchiya and Morinaga (Bio/Technology 6, 428–430 (1988)), in Eikmanns et al. (Gene 102, 93–98 (1991)), in European patent EP-B-0 472 869, in U.S. Pat. No. 4,601,893, in Schwarzer and Puhler (Bio/Technology 9, 84–87 (1991)), in Reinscheid et al. (Applied and Environmental Microbiology 60, 126–132 (1994)), in Labarre et al. (Journal of Bacteriology 175, 1001–1007 (1993)), in patent application WO 96/15246, in Malumbres et al. (Gene 134, 15–24 (1993)), in the Japanese patent document JP-A-10-229891, in Jensen and Hammer (Biotechnology and Bioengineering, 58, 191–195 (1998)), in Makrides (Microbiological Reviews, 60:512–538 (1996)) and in well-known textbooks on genetics and molecular biology.

An example of a plasmid with the help of which the sod gene can be overexpressed is pMM23 (FIG. 1) which is contained in the strain MH20-22B/pMM23. Plasmid pMM23 is an *E. coli-C. glutamicum* shuttle vector based on plasmid pBL1 (Ferandez-Gonzalez et al., Journal of Bacteriology 176(11), 3154–3161 (1994)), pACYC184 (Chang and Cohen, Journal of Bacteriology 134(3), 1141–1156 (1978)) and the trc promoter (Brosius et al. , Journal of Biological Chemistry 260, 3539–3541 (1985)) which carries the sod gene. Other plasmid vectors which can be replicated in *C. glutamicum* such as e.g. pEKEx1 (Eikmanns et al., Gene 102: 93–98 (1991)) or pZ8-1 (European patent 0 375 889) may be used in the same way as starting vectors for cloning and expressing the sod gene.

It may also be advantageous for the production of nucleotides, vitamins and in particular L-amino acids to overexpress one or more enzymes in the particular biosynthetic pathway in addition to the sod gene.

Thus, for example, for the preparation of nucleotides
the purF gene encoding for the glutamine PRPP-amidotransferase may be simultaneously overexpressed
the carAB gene encoding for carbamoyl phosphate synthetase may be simultaneously overexpressed.

Thus, for example, for the preparation of D-pantothenic acid
the panD gene encoding for aspartate decarboxylase (Dusch et al., Applied and Environmental Microbiology 65, 1530–1539 (1999)) may be simultaneously overexpressed.

Finally, for example, for the preparation of L-lysine
the dapA gene encoding for dihydrodipicolinate synthase may be simultaneously overexpressed (EP-B 0 197 335), or
a DNA fragment promoting S-(2-aminoethyl)-cysteine resistance may be simultaneously amplified (EP-A 0 088 166).

Furthermore it may be advantageous for the production of nucleotides, vitamins and in particular L-amino acids, quite particularly L-lysine, to switch off undesired side reactions apart from overexpression of the sod gene (Nakayama: "Breeding of Amino Acid Producing Micro-organisms", in Overproduction of Microbial Products, Krumphanzl, Sikyta, Vanek (eds.) Academic Press, London, UK, 1982).

The microorganisms prepared according to the invention may be cultivated continuously or batchwise in a batch process or a fed batch process or a repeated fed batch process for the purposes of producing metabolic products. A review of known cultivation methods is given in the textbook by Chmiel (Bioprozesstechnik 1. Einfuhrung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must satisfy the requirements of the particular strains in an appropriate manner. Descriptions of culture media for various microorganisms are given in the book "Manual of Methods for General Bacteriology" by the American Society for Bacteriology (Washington D.C., USA, 1981). Sugar and carbohydrates such as e.g. glucose, saccharose, lactose, fructose, maltose, molasses, starch and cellulose, oils and fats, such as e.g. soya oil, sunflower oil, peanut oil and coconut fat, fatty acids such as e.g. palmitic acid, stearic acid and linoleic acid, alcohols such as e.g. glycerol and ethanol and organic acids such as e.g. acetic acid can be used as sources of carbon. These substances may be used individually or as a mixture. Organic nitrogen-containing compounds such as peptones, yeast extract, meat extract, malt extract, maize steep water, soya bean meal and urea or inorganic compounds such as ammonium sulfate, ammonium chloride, ammonium phosphate, ammonium carbonate and ammonium nitrate may be used as sources of nitrogen. The sources of nitrogen may be used individually or as a mixture. Phosphoric acid, potassium dihydrogen phosphate or dipotassium hydrogen phosphate or the corresponding sodium-containing salts may be used as sources of phosphorus. The culture medium must also contain salts of metals such as e.g. magnesium sulfate or iron sulfate which are required for growth. Finally essential growth substances such as amino acids and vitamins may also be used in addition to the substances mentioned above. Over and above these, appropriate precursors may also be added to the culture medium. The feedstocks mentioned may be added to the culture as a one-off batch or may be supplied during cultivation in an appropriate manner.

Basic compounds such as sodium hydroxide, potassium hydroxide, ammonia or ammonia water or acid compounds such as phosphoric acid or sulfuric acid may be used in an appropriate manner to control the pH of the culture. Antifoam agents such as e.g. fatty acid polyglycol esters may be used to control the production of foam. To maintain the stability of plasmids, suitable selectively acting substances e.g. antibiotics may be added to the medium. In order to maintain aerobic conditions, oxygen or oxygen-containing gas mixtures such as e.g. air may be introduced into the culture. The temperature of the culture is generally 20° C. to 45° C. and preferably 25° C. to 40° C. Cultivation is continued until a maximum in the desired L-amino acid has been produced. This objective is normally achieved within 10 hours to 160 hours.

The following microorganisms were deposited at the German Collection of Microorganisms and Cell Cultures (DSMZ, Mascheroder Weg 1b, D-38124, Braunschweig, Germany) on Jun. 8, 1999 and in accordance with the Budapest treaty:

Esherichia coli strain XL1 blue/pMM23 as DSM 12860.

Corynebacterium melassecola strain 1019 as DSM 12859.

The process according to the invention is used for the fermentative preparation of nucleotides, vitamins and in particular L-amino acids with coryneform bacteria, quite particularly the preparation of L-lysine.

BRIEF DESCRIPTION OF THE DRAWINGS

FIG. 1.

FIG. 2.

The values for data relating to base pair numbers obtained are within the scope of reproducibility.

The abbreviations used are explained below:

| | |
|---|---|
| Ptrc: | trc promoter |
| Sod: | superoxide dismutase gene |
| cat: | chloramphenicol-resistant gene |
| ori pBL1: | replication region of the plasmid pBL1 |
| ori pACYC: | replication region of the plasmid pACYC184 |
| ori M13: | replication region of the phage M13 |
| bp: | base pair |
| NotI: | cutting point of the restriction endonuclease NotI |
| XbaI: | cutting point of the restriction endonuclease XbaI |
| BamHI: | cutting point of the restriction endonuclease BamHI |
| NcoI: | cutting point of the restriction endonuclease NcoI |
| SalI: | cutting point of the restriction endonuclease SalI |
| BglII: | cutting point of the restriction endonuclease BglII |
| NdeI: | cutting point of the restriction endonuclease NdeI |
| SmaI: | cutting point of the restriction endonuclease SmaI |
| PstI: | cutting point of the restriction endonuclease PstI |
| StuI: | cutting point of the restriction endonuclease StuI |
| XhoI: | cutting point of the restriction endonuclease XhoI |

DETAILED DESCRIPTION OF THE INVENTION

EXAMPLES

The following examples will further illustrate this invention.

Example 1

Cloning and Sequencing of the Sod Gene

1. Purification and Characterization of superoxide dismutase of Corynebacterium melassecola ATCC17965

For purification of superoxide dismutase, Corynebacterium melassecola ATCC17965 was grown aerobically on Bacto® Brain Heart Infusion medium (DIFCO Laboratories, Detroit, USA) at 34° C. until late exponential phase. Cells from one liter culture were harvested by centrifugation using an Avantiô J-25 centrifuge, and a JLA-10.500 rotor, of BECKMANN(Palo Alto, USA) at 5,000 g for 15 minutes at 4° C., and resuspended in a solution of 10 mM $MgCl_2$, 1 µg/ml Ribonuclease A, 1 g/ml Deoxyribonuclease I, 25 mM sodium phosphate buffer pH 7.5 to give a final optical density of 500 as measured by a DU 7400 spectrophotometer of BECKMAN (Palo Alto, USA) at a wavelength of 570 nm. For disruption, cells were passed three times though a Manual-Fill 40K cell (FA-030) with a FRENCH® presure cell press of SLM AMINCO® (Urbana, USA) at a shear force of 16,000 psi (110 MPa). The resulting extract was centrifuged using an Avantiô J-25 centrifuge and a JA-25.50 rotor of BECKMAN (Palo Alto, USA) at 10,000 g for 15 minutes at 4° C. The supernatant was ultracentrifuged using a L8-70M ultracentrifuge and a VTi 65.2 rotor of BECKMAN (Palo Alto, USA)at 130,000 g for 2 hours at 4° C. The supernatant was used as the crude extract.

From this step, purification of superoxide dismutase was followed by either activity staining after non denaturing gel electrophoresis as described by Schmidt et al. (European Journal of Biochemistry 156, 149–155 (1986)) or by the specific enzymatic assay described by Ukeda et al. (Analytical Biochemistry 251 (2), 206–209 (1997)), and by SDS-PAGE analysis as described by Laemmli (Nature 227, 680–685 (1970)). Protein content was estimated by the method of Lowry (Lowry et al., Journal of Biological Chemistry 193, 265–275 (1951)) using Bovine Immunoglobulin G as a standard.

The crude extract was precipitated for 30 minutes on ice by adding cristalline ammonium sulfate to a final saturation of 90%. The precipitate was collected by centrifugation at 10,000 g for 15 minutes at 4° C., using an Avanti6 J-25 centrifuge and a JA-25.50 rotor of BECKMAN (Palo Alto, USA), and discarded. The supernatant was adjusted to 100% ammonium sulfate saturation and the precipitate was collected by centrifugation as before. The pellet was dissolved in 10 ml 50 mM Tris-Cl buffer pH 8.0. This solution was dialysed for 24 hours against 2 liters of the same buffer. The protein solution was applied to a 2 ml Bioscale Q2 ion-exchange column of BIO-RAD (Hercules, USA), the column was washed with two colum volumes of 50 mM Tris-Cl buffer pH 8.0 and then eluted with a 0–0.5 M NaCl linear gradient. The active fractions were pooled, dialysed against 50 mM Tris-Cl buffer pH 8.0. The proteins were separated by gel filtration onto a 100 ml Sephacryl S300 column of PHARMACIA Biotech (St Quentin en Yvelines, France). All the chromatographic steps were performed with the FPLC BioLogic HR System of BIO-RAD (Hercules, USA). The active fractions were pooled and concentrated with Centricon®-30 concentrator cartridges from AMICON (Epernon, France). The final superoxide dismutase solution had a volume of 540 µl with a protein concentration of 0.2 mg/ml as estimated by the method of Lowry (Lowry et al., Journal of Biological Chemistry 193, 265–275 (1951)). Superoxide dismutase was estimated to be pure by SDS-PAGE analysis (Laemmli, Nature 227, 680–685 (1970)), and its subunit molecular weight was estimated to be 24.5 kDa.

Pure superoxide dismutase (10 µg) was isolated from a SDS-PAGE acrylamide gel within a slice. Protein was digested in gel slice with 0.2 µg of trypsin in 200 µl of 0.01% TWEEN 20, 0.1 M Tris-Cl buffer pH 8.6. Tryptic peptides were separated by a linear acetonitrile/0.1% Trifluoro Acetic Acid gradient onto a DEAE-C18 column with an 104A HPLC chromatography system of APPLIED BIOSYSTEMS (Foster City, USA). Two isolated peptides were sequenced with an APPLIED BIOSYSTEMS 473A Sequencer (Foster City, USA). These peptides have the following sequence:

peptide 15: NLAFNLGGHTNHSVF (SEQ ID NO:3)

peptide 18: FQDHFNSAALGLQGS (SEQ ID NO:4)

A comparison, using the BLAST programm (Altschul et al., Journal of Molecular Biology 215, 403–410 (1990)), of sequenced peptides with protein sequences in the National Center for Biotechnology Information (http://www.ncbi.nlm.nih.gov) database revealed high identities with superoxide dismutases of *Actinomyces viscosus* (100% identity, accession number X81381), *Corynebacterium diphteriae* (86% identity, accession number X813.82) for peptide 15, and *Corynebacterium diphteriae* (78% identity, accession number X81382) and *Corynebacterium pseudodiphteriticum* (73% identity, accession number X81383) for peptide 18.

2. Cloning of the Sod Gene

The molecular biology techniques used in cloning experiments were described by Ausubel et al. (Ausubel et al., in: Current protocols in molecular biology, John Wiley and sons (eds), New York, USA (1987)), except when otherwise stated. Molecular biology products were purchased by PROMEGA CORPORATION (Madison, USA) or BOEHRINGER MANNHEIM FRANCE S.A. (Meylan, France), except when specified.

To clone the sod gene encoding superoxide dismutase, a genomic DNA bank was constructed. *Corynebacterium melassecola* ATCC17965 was grown aerobically on Bacto® Brain Heart Infusion medium (DIFCO Laboratories, Detroit, USA) at 34° C. until late exponential phase. Cells from a 25 ml culture were harvested by centrifugation using an Avantiô J-25 centrifuge, and a JLA-10.500 rotor, of BECKMANN (Palo Alto, USA)at 5,000 g for 15 minutes at 4° C., resuspended in 3 ml of 10 mM Ethylene Diamine Tetra Acetate, 1% glucose, 20 mg/ml lysozyme, 25 mM Tris-Cl buffer pH 8.5, and incubated at 37° C. for 1 hour. Cell lysis was achieved by the addition of 6.5 ml of 1 mM Ethylene Diamine Tetra Acetate, 0.5% Sodium Dodecyl Sulfate, 1 mg/ml proteinase K, 10 mM Tris-Cl buffer pH 7.5, and incubation at 37° C. for 1 hour. To this suspension, 1.8 ml of 5M NaCl and 1.5 ml of 10% Cetyl Tridecyl Ammonium Bromide, 0.7 M NaCl solution were added. After incubation at 60° C. for 20 minutes, chromosomal DNA was extracted by gentle mixing with an equal volume of 24:1 V/V chloroform/isoamyl alcohol solution. Chromosomal DNA in the aqueous phase was precipitated with 0.6 volumes of isopropanol. The DNA precipitate was recovered by centrifugation at 10,000g for 15 minutes at 4° C., using an Avantiô J-25 centrifuge and a JA-25.50 rotor of BECKMAN (Palo Alto, USA), and resuspended in 1 mM EDTA, 10 mM Tris-Cl buffer pH 7.5. To 1 mg of chromosomal DNA diluted in the appropriate buffer, 15 units of restriction enzyme Mbo I were added, and the mix incubated for 1 hour at 37° C. Partially restricted DNA was size-fractionated by ultracentrifugation in a 10–40% W/V sucrose gradient, using a L8-70M ultracentrifuge and a SW40Ti rotor of BECKMAN (Palo Alto, USA) at 80,000 g for 17 hours at 20° C. Chromosomal DNA fragments in the size range 6 to 10 kb, as estimated by horizontal agarose gel electrophoresis, were recovered and pooled. The selection-positive cloning vector pUN121 (Nilsson et al., Nucleic Acids Research 11, 8019–8030 (1983)) was linearized by the restriction enzyme Bcl I. To 1 µg of linearized pUN 121, 2 µg of Mbo I-generated chromosomal DNA fragments from *Corynebacterium melassecola* ATCC17965 were added in a ligation mixture containing 0.1 unit T4 DNA ligase, incubated for 24 hours at 16° C. The ligation mixture was then used to transform the *Escherichia coli* strain DH5α (Hanahan, Journal of Molecular Biology 166, 557–580 (1983)) by electroporation as described by Bonamy et al.(Bonamy et al., FEMS Microbiology Letters 66, 263–270 (1990)). Transformants were recovered after incubation on 10 µg/ml tetracycline-containing Bacto® Luria Bertani agar (DIFCO Laboratories, Detroit, USA) plates for 24 hours at 37° C. More than 10,000 independant transformant clones were obtained, indicating from Clarke and Carbon (Clarke and Carbon, Cell 9, 91–99 (1976)) any *Corynebacterium melassecola*-issued chromosomal DNA fragment to be present at least one time in this DNA bank with a 99.9% probability. Transformants were picked-up individually and cultivated for 24 hours at 37° C. in 25 µl of LB liquid medium, containing 100 µg/ml ampicillin, in 96-wells microtitration plates. All the transformants were replica-plated on AMERSHAM Hybondô-N nylon membranes from AMERSHAM (Little Chalfont, England) and allowed to grow for 24 hours at 37° C. Colonies were lysed onto membranes. Master microtitration plates were stored at −80° C. until use, after each well was completed to 50 µl with 25 µl of 80% glycerol.

Screening of the *Corynebacterium melassecola* ATCC 17965 DNA bank for the presence of the sod gene was achieved by DNA/DNA hybridization with a sod-specific radioactive probe as described by Ausubel et al. (Ausubel et al., in: Current protocols in molecular biology, John Wiley and sons (eds), New York, USA (1987)). The sod-specific DNA probe was prepared as follows. Taking into account the codon bias index for highly expressed genes in Corynebacterium species (Malumbres et al., Gene 134, 15–24 (1993)), degenerated oligonucleotides S1 and S2 were designed on the basis of peptide 15 and peptide 18 sequences respectively. An additional oligonucleotide, namely S3 was designed from the peptide DMWEHAFYL. These oligonucleotides had the following sequences:

S1 5' GGCCACACCAACCACTCCGTSTT 3' (SEQ ID NO:5)

S2 5' GAGTTGAAGTGRTCCTGGAACTT 3' (SEQ ID NO:6)

S3 5' AGGTAGAAWGCGTGCTCCCACAT 3' (SEQ ID NO:7)

(single letter code : S=C or G, R=A or G, W=A or T)

Oligonucleotide were synthesed with a Polygen DNA synthetiser of POLYGEN GmbH (Langen, Germany). These oligonucleotides were used to amplify a DNA fragment in a Polymerase Chain Reaction experiment, with *Corynebacterium melassecola* ATCC 17965 chromosomal DNA, prepared as before, as the template. This experiment was performed in a Crocodile II microprocessor controlled incubation system of APPLIGENE ONCOR (Illkirch, France), with Ampli Taq Gold polymerase and its buffer from PERKIN ELMER (Foster City, USA) as follows:

Chromosomal DNA 30 ng oligonucleotide S1 0.5 µM oligonucleotide S2 or S3 0.5 µM

Ampli Taq Gold 2.5 units

Buffer ×10 5 µl

Water to 50 µl final volume

Polymerase chain Reaction consisted in 10 minutes incubation at 94° C., followed by 35 amplification cycles (1 minute denaturation at 94° C., 1 minute annealling at 50° C., 1 minute polymerisation at 72° C. for each cycle). The size of amplified DNA fragments, as estimated by agarose gel electrophoresis, was close to what expected from nucleotide sequence data of known sod genes. Amplification with oligonucleotides S1 and S2 gave a fragment of about 130 nucleotides, and amplification with oligonucleotides S1 and S3 a fragment of about 290 nucleotides. Both amplified fragments were cloned into the specialized vector pGEM®-T of PROMEGA CORPORATION (Madison, USA) to give plasmids pMM6 and pMM7. Plasmid pMM6 contained the fragment amplified with S1 and S2, pMM7 contains the fragment amplified with S1 and S3. Inserted fragments were sequenced by the dideoxynucleotide chain termination method of Sanger et al. (Sanger et al., Proceedings of the National Academy of Science USA 74, 5463–5467 (1977)), with oligonucleotide S1 as the primer. DNA sequencing was performed with a Model 373 DNA sequencing system of APPLIED BIOSYSTEM (Foster City, USA). DNA sequence analysis confirmed that both fragments corresponded to fragments of a superoxide dismutase-encoding gene.

The origin of the amplified fragment obtained with S1 and S3 as primers was controlled by Southern experiment (Southern, Journal of Molecular Biology 98, 503–517 (1975)) as follows. Chromosomal DNA of Corynebacterium melassecola ATCC 17965 and from *Escherichia coli* DH5a (Hanahan, Journal of Molecular Biology 166, 557–580 (1983)) were restricted with enzymes Hind III, Pst I or Pvu II. DNA fragments were separated by horizontal agarose gel electrophoresis, blotted onto a AMERSHAM Hybondô-N nylon membrane from AMERSHAM (Little Chalfont, England). Oligonucleotides S1 and S3 were used to amplify, by polymerase chain reaction as described before with pMM7 as the template, a sod-specific DNA fragment. This fragment was radioactively labelled with $\alpha^{32}p$ dCTP with the T7 QuickPrimeô Kit of PHARMACIA Biotech (St Quentin en Yvelines, France). Labelling was performed as indicated by the furnisher. The radioactive probe specifically hybridized with *Corynebacterium melassecola* ATCC 17965 chromosomal DNA.

This labelled DNA probe was also used to screen the *Corynebacterium melassecola* ATCC 17965 genomic library previously plated onto nylon membranes. From this screening, six colonies were first selected. Plasmids were isolated from the respective clones and analysed by restriction analysis and polymerase chain reaction. Plasmid pMM8 was selected for further studies because it contains a 10-kbp recombinant DNA fragment that hybridize with the radioactive probe derived from pMM7, from which a 290 nucleotides fragment was amplified by polymerase chain reaction with oligonucleotides S1 and S3 as primers.

3. Sequencing of the Sod Gene

The sod locus in plasmid pMM8 was sequenced by the dideoxynucleotide chain termination method of Sanger et al. (Sanger et al., Proceedings of the National Academy of Science USA 74, 5463–5467 (1977)) on a a Model 373 DNA sequencing system of APPLIED BIOSYSTEM (Foster City, USA). Sequencing started from oligonucleotide S1 as a primer in one direction and oligonucleotide S3 in the other one.

Sequence determination proceeded to completion on the two strands by a "DNA walking" strategy, new oligonucleotides beeing designed from previously determined nucleotide sequences and synthetized as described before. The nucleotide sequence was computer-analysed using the program Gene Jockey II, Sequence Processor provided by BIOSOFT (Cambridge, UK). The sequence is shown as SEQ ID NO.1. A major open reading frame of 603 nucleotides was thus identified. This open reading frame corresponds to a 200 amino acids protein (SEQ ID NO.2). This deduced protein has a calculated molecular weight of 22,103 da, close to the experimental value determined for superoxide dismutase protein by SDS-Page electrophoresis (See above).

Experimentally determined peptide 15 and peptide 18 sequences are found within the deduced protein sequence. Moreover, the deduced protein shows extensive identity to other completely sequenced superoxide dismutases as seen from comparisons with sequences in the National Center for Biotechnology Information (URL:http://www.ncbi.nlm.nih.gov) database. *Corynebacterium melassecola* ATCC 17965 superoxide dismutase shows identities with those of *Nocardia asteroides* (65% identity, accession number U02341), *Mycobacterium fortuitum* (63% identity, accession number X70914), *Mycobacterium avium* (63% identity, accession number U 11550), *Mycobacterium leprae* (61% identity, accession number X16453) and *Mycobacterium tuberculosos* (60% identity, accession number X52861).

Example 2

Expression of the Sod Gene

1. Cloning of the Sod Gene into an Expression Vector

For expression of the sod gene the expression vector pMM23 was constructed starting from pCGL482.

Figure 2:
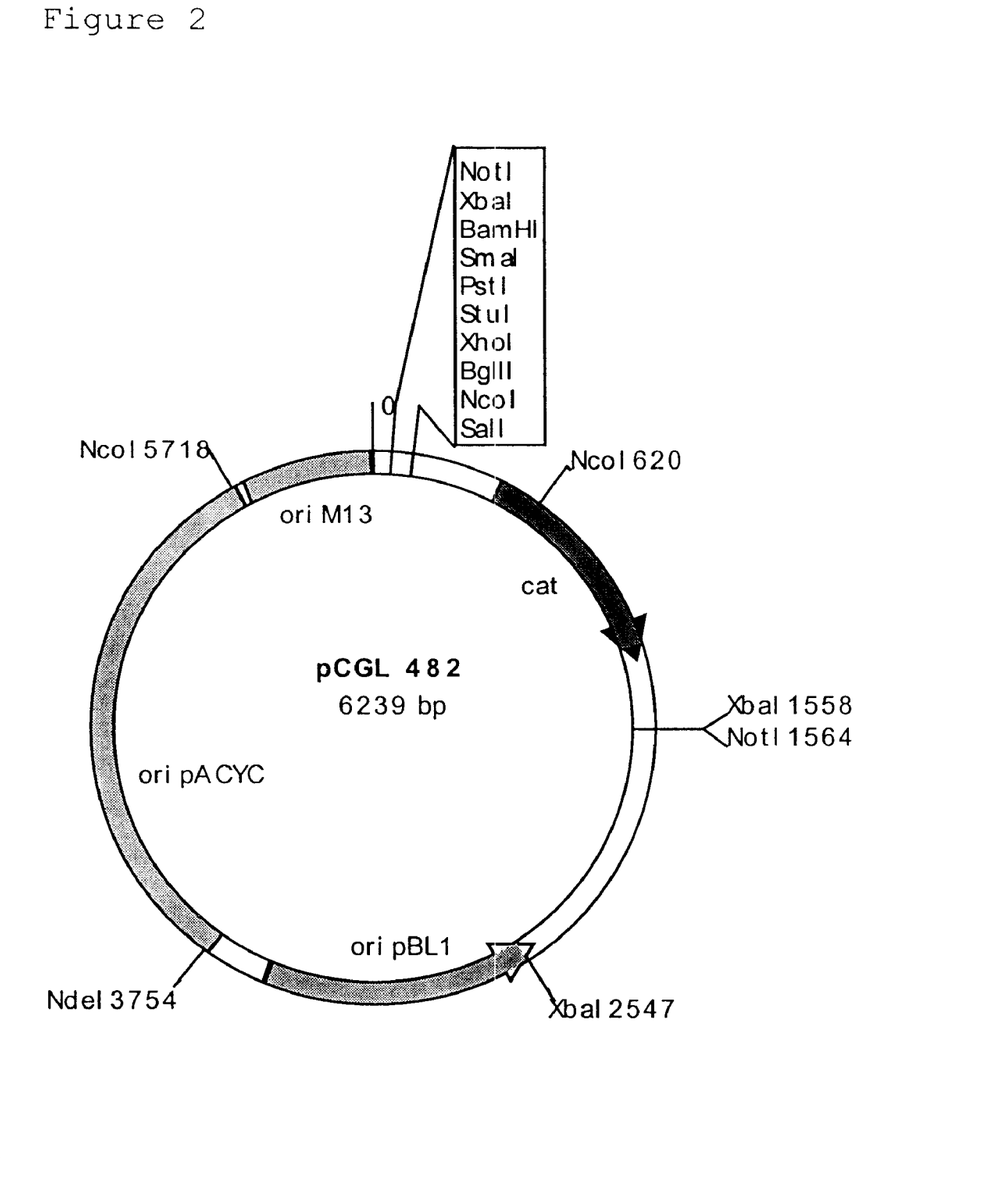
FIG. 2 is a diagrammatic representation of the plasmid pCGL482.

Plasmid pCGL482 (FIG. 2) is an *Escherichia coli-Corynebacterium glutamicum* shuttle vector composed of segments of pACYC184 (Chang and Cohen, Journal of Bacteriology 134(3), 1141–1156 (1978)), pBL1 (Ferandez-Gonzalez et al., Journal of Bacteriology 176(11), 3154–3161 (1994)), the origine of replication of phage M13 (Rashed and Oberer, Microbiological Review 50, 401–427, (1986))), a multiple cloning site and the chloramphenicol resistance gene of pACYC184 as selection marker.

Figure 1:
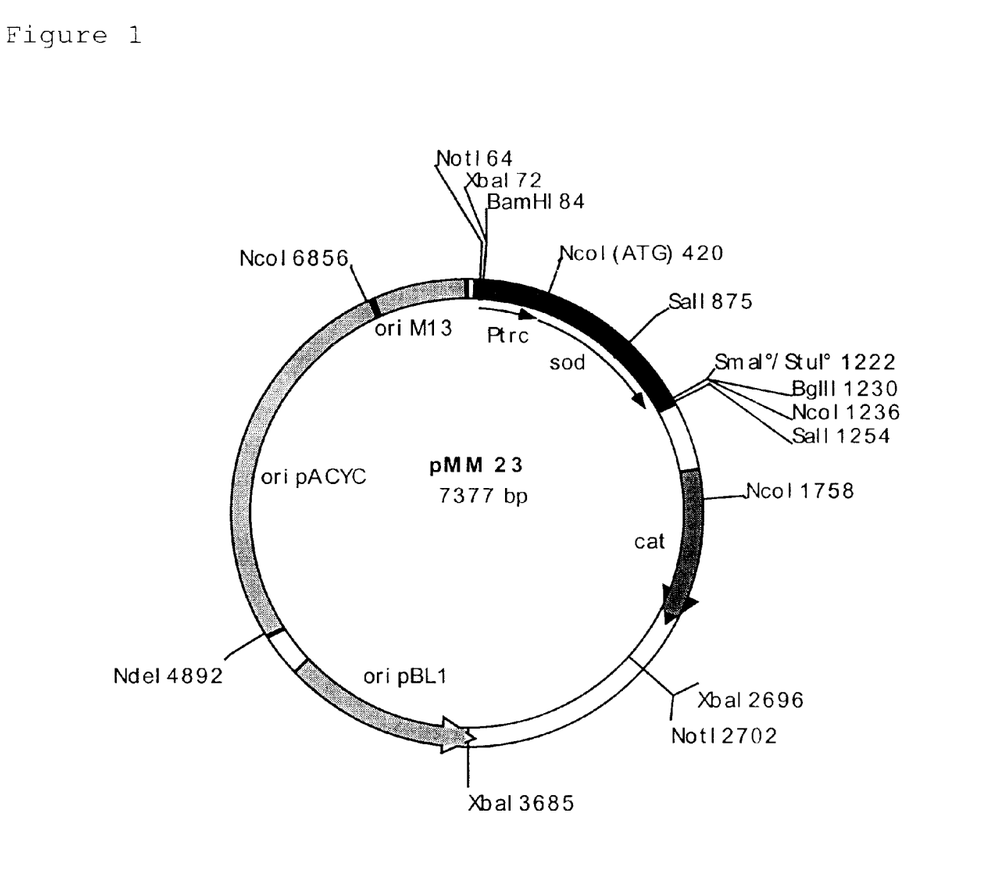
FIG. 1 is a diagrammatic representation of the plasmid pMM23.

DNA of pCGL482 was digested with restriction enzymes BamHI and StuI. Plasmid pMM8 was digested with NcoI and SmaI and the 0.8 kbp DNA fragment comprising the sod gene isolated by agarose gel electrophoresis. Plasmid pKK388-1 (Brosius, in Vector: A survey of molecular cloning vectors and their uses, Rodrigez Editor, pp 205–225, Butterworth Boston, USA (1988))was digested with BamHI and NcoI and the 0.36 kbp DNA fragment encompassing the trc promoter (Brosius et al., Journal of Biological Chemistry 260, 3539–3541 (1985)) isolated by agarose gel electrophoresis. The three components were mixed and treated with T4-DNA-ligase. The ligation mixture was used to transform *Escherichia coli* strain XL1-Blue (Bullock et al., BioTechniques 5, 376–378 (1987))) by electroporation as described by Bonamy et al.(Bonamy et al., FEMS Microbiology Letters 66, 263–270 (1990)). Transformants were selected by incubation on Bacto® Luria Bertani agar (DIFCO Laboratories, Detroit, USA) supplemented with chloramphenicol (30 µg/ml) for 2 days at 37° C. Plasmid DNA was isolated from one single colony and designated pMM23 (FIG. 1).

*C. melassecola* strain 1019 (deposited under DSM 12859) which is a restriction deficient mutant derived from strain ATCC 17965 was transformed with plasmids pCGL482 and pMM23 as described by Bonamy et al. (Bonamy et al., FEMS Microbiology Letters 66, 263–270 (1990)). Transformants were selected on Bacto® Brain Heart Infusion agar (DIFCO Laboratories, Detroit, USA) supplemented with chloramphenicol (6 µg/ml) incubated at 34° C. for 2 days.

2. Enzyme Measurements

Strains 1019, 1019/pCGL482 and 1019/pMM23 were grown aerobically on Bacto® Brain Heart Infusion medium (DIFCO Laboratories, Detroit, USA) supplemented with chloramphenicol for the latter two strains at 34° C. until the mid exponential phase. Strains were harvested by centrifugation using a Megafuge 1.0 R centrifuge of HERAUS Instruments GmbH (Hanau, Germany) at 5,000 g for 15 minutes and resuspended in 50 mM sodium phosphate buffer pH 8.0 to give a final optical density of 50 as measured by a DU 7400 photometer of BECKMAN (Palo Alto, USA) at a wavelength of 570 nm.

The cells were mechanically disrupted with glass beads. A volume of 1 ml cell suspension was mixed with 1 g of glass beads having a diameter of 0,5 mm in a 2 ml Eppendorf tube. The suspension was vortexed for 2 minutes and then incubated on ice for 2 minutes. This procedure was repeated three times. The resulting suspension was centrifuged for at least 15 minutes at 13,000 rpm using a Sigma 113 centrifuge of SIGMA (St Louis, USA). The supernatant was used for enzyme assays.

Superoxide dismutase assays were performed as described by Ukeda et al. (Analytical Biochemistry 251(2), 206–209 (1997)) using Escherichia coli Mn dependent superoxide dismutase obtained from SIGMA-ALDRICH (St Quentin Fallavier, France) as a standard. Estimations of protein concentration were performed by the method of Lowry (Lowry et al., Journal of Biological Chemistry 193, 265–275 (1951)) using Bovine Immunoglobulin G as a standard. The results are shown in table 1. One enzyme unit is defined as the amount of enzyme that inhibit the rate of reduction of cytochrome c by 50% in a coupled system with xanthine and xanthine oxidase at pH 7.8 and 25° C.

TABLE 1

| Strain | Superoxide dismutase Activity units/mg protein |
| --- | --- |
| 1019 | 16 |
| 1019/pCGL482 | 13 |
| 1019/pMM23 | 56 |

What is claimed is:

1. An isolated DNA comprising a nucleotide sequence encoding a protein with superoxide dismutase (sod) activity wherein said protein has the amino acid sequence of SEQ ID NO:2.

2. An isolated DNA comprising the nucleotide sequence of SEQ ID NO:1 and wherein said DNA encodes a protein with superoxide dismutase activity.

3. An isolated DNA, wherein said DNA has a sequence consisting of that of SEQ ID NO:1 and wherein said DNA encodes a protein with superoxide dismutase activity.

4. An isolated DNA, wherein said DNA has a sequence consisting of that of nucleotides 339 to 937 of SEQ ID NO:1 and wherein said sequence encodes a protein with superoxide dismutase activity.

5. A vector for expressing a protein with superoxide dismutase activity, said vector comprising the isolated DNA of any one of claims 1–4, and a promoter linked to said isolated DNA.

6. A *C. glutamicum* bacterium transformed with the vector of claim 5.

7. A process for the production of an amino acid comprising:
 (a) fermenting the *C. glutamicum* bacterium of claim 6; and
 (b) isolating said amino acid from the culture medium or bacterium of step (a).

8. The process of claim 7, wherein said amino acid is L-lysine.

9. The plasmid pMM23 deposited under deposit number DSM 12860.

10. A *C. glutamicum* bacterium transformed with the plasmid of claim 9.

11. A process for the production of an amino acid comprising:
(a) fermenting the *C. glutamicum* bacterium of claim 10; and
(b) isolating said amino acid from the culture medium or bacterium of step (a).

12. The process of claim 11, wherein said amino acid is L-lysine.

* * * * *

SEQUENCE LISTING

<160> NUMBER OF SEQ ID NOS: 7

<210> SEQ ID NO 1
<211> LENGTH: 1143
<212> TYPE: DNA
<213> ORGANISM: Corynebacterium melassecola
<220> FEATURE:
<221> NAME/KEY: CDS
<222> LOCATION: (338)..(937)

<400> SEQUENCE: 1

```
ggatccggcc aatgcttctg gcgtcaggca gccatcggaa gctgtggtat ggctgtgcag      60
gtcgtaaatc actgcataat tcgtgtcgct caaggcgcac tcccgttctg gataatgttt     120
tttgcgccga catcataacg gttctggcaa atattctgaa atgagctgtt gacaattaat     180
catccggctc gtataatgtg tggaattgtg agcggataac aatttcacac aggaaacagc     240
gccgctgaga aaaagcgaag cggcactgct ctttaacaat ttatcagaca atctgtgtgg     300
gcactcgacc ggaattatcg ataaggaggt ttaaacc atg gct gta tac gaa ctc     355
                                           Met Ala Val Tyr Glu Leu
                                            1               5 cca gaa ctc gac tac gca tac gac gct ctc gag cca cac atc gcc gct     403
Pro Glu Leu Asp Tyr Ala Tyr Asp Ala Leu Glu Pro His Ile Ala Ala
             10                  15                  20 gaa atc atg gag ctt cac cac tcc aag cac cac gca acc tac gtt gca     451
Glu Ile Met Glu Leu His His Ser Lys His His Ala Thr Tyr Val Ala
         25                  30                  35 ggc gca aac gca gca ctc gag gca cta gag aag gca cgc gaa gag ggc     499
Gly Ala Asn Ala Ala Leu Glu Ala Leu Glu Lys Ala Arg Glu Glu Gly
     40                  45                  50 acc aac cct gac cag atc cgt gca ctg tcc aag aac ctt gca ttc aac     547
Thr Asn Pro Asp Gln Ile Arg Ala Leu Ser Lys Asn Leu Ala Phe Asn
 55                  60                  65                  70 ctc ggt gga cac acc aac cac tcc gtt ttc tgg aag aac ctc tcc cct     595
Leu Gly Gly His Thr Asn His Ser Val Phe Trp Lys Asn Leu Ser Pro
                 75                  80                  85 aac ggt ggc ggc gag cct acc ggc gaa ctg gct gag gct atc aac cgc     643
Asn Gly Gly Gly Glu Pro Thr Gly Glu Leu Ala Glu Ala Ile Asn Arg
             90                  95                 100 gac ttc ggt tct ttc gct aag ttc cag gat cac ttc aac tct gca gca     691
Asp Phe Gly Ser Phe Ala Lys Phe Gln Asp His Phe Asn Ser Ala Ala
            105                 110                 115
```

```
ctc ggc ctg cag ggc tcc ggc tgg gcg gtt ctc ggc tac gac cac atc         739
Leu Gly Leu Gln Gly Ser Gly Trp Ala Val Leu Gly Tyr Asp His Ile
    120                 125                 130 tcc ggt cgc ctg gtt atc gag cag ctc acc gac cag cag ggc aac atc         787
Ser Gly Arg Leu Val Ile Glu Gln Leu Thr Asp Gln Gln Gly Asn Ile
135                 140                 145                 150 tcc gtc gac atc acc cca gtt ctg atg ctc gat atg tgg gag cac gct         835
Ser Val Asp Ile Thr Pro Val Leu Met Leu Asp Met Trp Glu His Ala
                155                 160                 165 ttc tac ctg cag tac aag aac gtt aag gca gat tac gtc aag gct gtt         883
Phe Tyr Leu Gln Tyr Lys Asn Val Lys Ala Asp Tyr Val Lys Ala Val
            170                 175                 180 tgg aac gtc ttc aac tgg gac gac gca gca gca cgc ttc gca gca gct         931
Trp Asn Val Phe Asn Trp Asp Asp Ala Ala Ala Arg Phe Ala Ala Ala
        185                 190                 195 tcc aag taagcatttt tagtacgtgc aataaccact ctggttttc cagggtggtt          987
Ser Lys
    200 ttttgatgcc cttttggag tcttcaactg ggtagcgtta ggattcacca tttccggcgg       1047 gcatccggcg aaaaatggtg aatccacaca ctgttgccgg gcagtaagta cttttcgccg       1107 accccgatcg ctaggccagc tgtggcaagc cccggg                                 1143

<210> SEQ ID NO 2
<211> LENGTH: 200
<212> TYPE: PRT
<213> ORGANISM: Corynebacterium melassecola

<400> SEQUENCE: 2

Met Ala Val Tyr Glu Leu Pro Glu Leu Asp Tyr Ala Tyr Asp Ala Leu
1               5                   10                  15

Glu Pro His Ile Ala Ala Glu Ile Met Glu Leu His His Ser Lys His
                20                  25                  30

His Ala Thr Tyr Val Ala Gly Ala Asn Ala Ala Leu Glu Ala Leu Glu
            35                  40                  45

Lys Ala Arg Glu Glu Gly Thr Asn Pro Asp Gln Ile Arg Ala Leu Ser
50                  55                  60

Lys Asn Leu Ala Phe Asn Leu Gly Gly His Thr Asn His Ser Val Phe
65                  70                  75                  80

Trp Lys Asn Leu Ser Pro Asn Gly Gly Gly Glu Pro Thr Gly Glu Leu
                85                  90                  95

Ala Glu Ala Ile Asn Arg Asp Phe Gly Ser Phe Ala Lys Phe Gln Asp
            100                 105                 110

His Phe Asn Ser Ala Ala Leu Gly Leu Gln Gly Ser Gly Trp Ala Val
        115                 120                 125

Leu Gly Tyr Asp His Ile Ser Gly Arg Leu Val Ile Glu Gln Leu Thr
    130                 135                 140

Asp Gln Gln Gly Asn Ile Ser Val Asp Ile Thr Pro Val Leu Met Leu
145                 150                 155                 160

Asp Met Trp Glu His Ala Phe Tyr Leu Gln Tyr Lys Asn Val Lys Ala
                165                 170                 175

Asp Tyr Val Lys Ala Val Trp Asn Val Phe Asn Trp Asp Asp Ala Ala
            180                 185                 190

Ala Arg Phe Ala Ala Ala Ser Lys
        195                 200

<210> SEQ ID NO 3
```

-continued

```
<211> LENGTH: 15
<212> TYPE: PRT
<213> ORGANISM: Corynebacterium melassecola

<400> SEQUENCE: 3

Asn Leu Ala Phe Asn Leu Gly Gly His Thr Asn His Ser Val Phe
 1               5                  10                  15

<210> SEQ ID NO 4
<211> LENGTH: 15
<212> TYPE: PRT
<213> ORGANISM: Corynebacterium melassecola

<400> SEQUENCE: 4

Phe Gln Asp His Phe Asn Ser Ala Ala Leu Gly Leu Gln Gly Ser
 1               5                  10                  15

<210> SEQ ID NO 5
<211> LENGTH: 23
<212> TYPE: DNA
<213> ORGANISM: Artificial Sequence
<220> FEATURE:
<223> OTHER INFORMATION: Description of Artificial
      Sequence:oligonucleotide probe

<400> SEQUENCE: 5
ggccacacca accactccgt stt                                          23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial
      Sequence:oligonucleotide probe

<400> SEQUENCE: 6
gagttgaagt grtcctggaa ctt                                          23

<210> SEQ ID NO 7
<211> LENGTH: 23
<212> TYPE: DNA
<213> ORGANISM: Artificial Sequence
<220> FEATURE:
<223> OTHER INFORMATION: Description of Artificial
      Sequence:oligonucleotide probe

<400> SEQUENCE: 7
aggtagaawg cgtgctccca cat                                          23
```